United States Patent
Franzosi et al.

(10) Patent No.: US 10,889,841 B2
(45) Date of Patent: Jan. 12, 2021

(54) OLEAGINOUS YEAST VARIANT, METHOD FOR OBTAINING THEREOF AND USE THEREOF FOR LIPID PRODUCTION

(71) Applicant: ENI S.p.A., Rome (IT)

(72) Inventors: Giuliana Franzosi, Novara (IT); Daniela Cucchetti, Cuggiono (IT); Daniele Bianchi, Arese (IT); Silvia Galafassi, Laveno Mombello (IT); Concetta Compagno, Spino D'adda (IT)

(73) Assignee: ENI S.p.A., Rome (IT)

( * ) Notice: Subject to any disclaimer, the term of this patent is extended or adjusted under 35 U.S.C. 154(b) by 22 days.

(21) Appl. No.: 16/262,554

(22) Filed: Jan. 30, 2019

(65) Prior Publication Data

US 2019/0161778 A1 May 30, 2019

Related U.S. Application Data

(62) Division of application No. 15/540,121, filed as application No. PCT/IB2015/060031 on Dec. 29, 2015, now Pat. No. 10,301,656.

(30) Foreign Application Priority Data

Dec. 31, 2014 (IT) .............. MI2014A2292

(51) Int. Cl.
  *C12P 7/26* (2006.01)
  *C12P 7/64* (2006.01)
  *C12R 1/645* (2006.01)
  *C12N 1/16* (2006.01)

(52) U.S. Cl.
  CPC ............ *C12P 7/6463* (2013.01); *C12R 1/645* (2013.01); *C12N 1/16* (2013.01); *C12P 2203/00* (2013.01)

(58) Field of Classification Search
  CPC .... C12P 7/6463; C12P 2203/00; C12R 1/645; C12N 1/16
  See application file for complete search history.

(56) References Cited

U.S. PATENT DOCUMENTS

2014/0329287 A1    11/2014   Blazeck et al.

FOREIGN PATENT DOCUMENTS

| WO | WO 2009/124694 A2 | 10/2009 |
| WO | WO 2014/179748 A2 | 11/2014 |

OTHER PUBLICATIONS

Morales et al., FEMS Microbiology Letters, vol. 69, pp. 73-78, 1990.*
Capusoni et al., Bioresource Technology, vol. 238, pp. 281-289, 2017.*
Written Opinion of the International Searching Authority dated Mar. 17, 2016 in PCT/IB2015/060031.
International Search Report dated Mar. 17, 2016 in PCT/IB2015/060031.
Rui P. Oliveira, et al., "isolation and Characterisation of mutants from the halotolerant yeast *Pichia sorbitophila* defective in H$^+$glycerol symport activity", FEMS Microbiology Letters, vol. 142, XP055210286, Jan. 1, 1996, pp. 1-9.
Silvia Galafassi, et al., "Lipid Production for Second generation biodiesel by the oleaginous yeast *Rhodotorula graminis*", Bioresource Technology, vol. 111, XP028474433, Feb. 8, 2012, pp. 398-403.

* cited by examiner

*Primary Examiner* — Richard G Hutson
(74) *Attorney, Agent, or Firm* — Oblon, McClelland, Maier & Neustadt, L.L.P.

(57) ABSTRACT

The present invention concerns an oleaginous yeast variant of the species *Rhodosporidium azoricum* characterized by higher biomass yields and intra-cellular lipid accumulation useful for the production of bio-fuels higher, in determined conditions, with respect to the wild type strain of the same species.
Furthermore, the invention concerns a method through which said oleaginous yeast variant of the species *Rhodosporidium azoricum* was obtained.
The invention further concerns the lipid production by means of said variant strain of oleaginous yeast of the species *Rhodosporidium azoricum*.

7 Claims, No Drawings

OLEAGINOUS YEAST VARIANT, METHOD FOR OBTAINING THEREOF AND USE THEREOF FOR LIPID PRODUCTION

CROSS REFERENCE TO RELATED APPLICATIONS

This application is a divisional application of prior U.S. application Ser. No. 15/540,121 filed Jun. 27, 2017, the disclosure of which is incorporated herein by reference in its entirety. U.S. application Ser. No. 15/540,121 is the national stage of PCT/IB2015/060031 filed Dec. 29, 2015, the disclosure of which is incorporated herein by reference in its entirety. U.S. application Ser. No. 15/540,121 claims priority to Italian Application No. MI2014A002292 filed Dec. 31, 2014, the disclosure of which is incorporated herein by reference in its entirety.

The present invention relates to the field of biotechnology. Particularly, the present invention concerns an oleaginous yeast variant of the species *Rhodosporidium azoricum* characterized by higher biomass yields and intra-cellular lipid accumulation, in determined conditions, with respect to the wild-type strain of the same species.

Furthermore, the invention concerns a method through which said oleaginous yeast variant of the species *Rhodosporidium azoricum* was obtained.

The invention further concerns the lipid production by means of said variant strain of oleaginous yeast of the species *Rhodosporidium azoricum*.

Lipids so obtained may be advantageously used as synthesis intermediates, particularly in the field so-called "green-chemistry", or in the biofuels production such as, for example, "biodiesel" or "green diesel", which may be used as such, or in mixture with other motor-fuels.

Lipids production by microbial processes is an advantageous alternative to the current production methods from renewable sources. Compared to lipid extraction from plant, microbial processes are cheaper from the economic point of view, because they are scalable in a more easy way, they require less manpower, and they take advantage of the microorganism property of rapid reproduction on low-cost substrates such as, for example, derivatives from the hydrolysis of lignocellulosic materials. Furthermore, they are independent from climatic factors and do not compete with agricultural exploitation of soil for alimentary purposes.

For this purpose, oleaginous yeasts are particularly promising, namely yeasts which are capable to accumulate lipids in specific cultivation conditions, especially triglycerides, for over the 25% of their dry weight. The use of oleaginous yeasts for lipid production is known in the art [Meng X., Yang J., Xu X., Zhang L., Nie Q., Xian M. (2009), "Biodiesel production from oleaginous microorganisms", *Renewable Energy*, vol. 34, p. 1-5; Galafassi S., Cucchetti D., Pizza F., Franzosi G., Bianchi D., Compagno C. (2012), "Lipid production for second generation biodiesel by the oleaginous yeast *Rhodotorula graminis*". *Bioresource Technol.*, vol. 111, p. 398-403].

Nevertheless, some limitations referred to the use of oleaginous yeasts, which are related to their mechanisms of metabolic control are described. It was demonstrated that some species of oleaginous yeast may accumulate lipids up to 60% of their weight, however the accumulation is inhibited by high concentrations of some nutrients normally included in the culture medium for promoting biomass production (such as, for example, nitrogen, sulfur, and phosphorous sources). In fact, in the art is disclosed that the intracellular accumulation of lipids significantly increases as, with the progress of the culture of these oleaginous yeasts, the molar ratios between carbon and nitrogen (C/N), or between carbon and sulfur (C/S), or between carbon and phosphorous (C/P) in the culture medium balance in favor of carbon [Granger L.-M., Perlot P., Goma G., Pareilleux A. (1993) "Effect of various nutrient limitations on fatty acid production by *Rhodotorula glutinis*". *Applied Microbiology and Biotechnology*, vol. 38 (6), p. 784-789; Wu S., Hu C., Jin G., Zhao X., Zhao Z. K. (2010) "Phosphate-limitation mediated lipid production by *Rhodosporidium toruloides*". *Bioresource Technol.*, vol. 101, p. 6124-6129; Wu S., Zhao X., Shen H., Wang Q., Zhao Z. K. (2011), "Microbial lipid production by *Rhodosporidium toruloides* under sulfate-limited conditions". *Bioresource Technol.*, vol. 102, p. 1803-1807].

In order to overcome such limitation and therefore supporting lipid accumulation inside these yeasts cells, fermentative set-ups and culture conditions which provide limiting concentrations of nitrogen in the culture medium were developed [Zhao X., Hu C., Wu S., Shen, H., Zhao Z. K. (2011), "Lipid production by *Rhodosporidium toruloides* Y4 using different substrate feeding strategies", *J. Ind. Microbiol. Biotechnol.*, vol. 38 (5), p. 627-632; Li Y., Zhao Z. K., Bai F. (2007), "High-density cultivation of oleaginous yeast *Rhodosporidium toruloides* Y4 in fed-batch culture", *Enzyme Microbial Technology*, vol. 41 p. 312-317].

In the cited documents, in order to contrast the negative effect of nutrient sources deficiency on biomass yield, authors use very laborious fermentative procedures, which provide the use of culture media with defined composition and high costs. All that limits the exploitation of these procedures for industrial purposes.

The Applicant has thus faced the problem of providing an oleaginous yeast capable to significantly accumulate lipids inside the cell regardless of the method of fermentation and using culture media from not-selected sources, such as, for example, hydrolyzates of lignocellulosic material, so that the cultivation of said yeast allows to obtain high yields of lipids, without using laborious and uneconomical culture methods.

Applicant has now found an oleaginous yeast which overcomes the limitation of the prior art.

Specifically, the invention concerns a variant of *Rhodosporidium azoricum*, deposited on Oct. 10, 2014 according to the Budapest Treaty at Leibniz-Institut DSMZ—Deutsche Sammlung von Mikroorganismen und Zellkulturen GmbH—Inhoffenstraße 7 B 38124 Braunschweig (Germany), deposit number DSM 29495, which demonstrated intracellular accumulation yields of lipids significantly higher than the wild-type strain of the same species of *Rhodosporidium azoricum* when cultivated in a culture medium enriched in nitrogen sources.

According to a second aspect, the invention relates to a method for obtaining mutagenized oleaginous yeasts which allowed the selection of the variant *Rhodosporidium azoricum* DSM 29495. Such method may be advantageously used to produce, through random mutagenesis techniques, and isolating hyperaccumulator variants of oleaginous yeast strains.

A further aspect of the present invention relates to a production process of lipids through the cultivation of said variant *Rhodosporidium azoricum* DSM 29495. According to a preferred embodiment of the present invention, said process is carried out in a fed-batch fermenter in which a derivative of the lignocellulosic material hydrolysis is used as substrate.

For the purposes of the present description and the following claims, the definitions of the numeric ranges always comprise extremes unless otherwise specified.

For the purposes of the present description and the following claims, the term "comprising" also includes the terms "which consists essentially of" or "which consist of".

For the purposes of the present invention, with the term "biodiesel" it is intended a fuel for diesel engines comprising alkyl esters (such as, for example, methyl, propyl or ethyl esters) of long chain fatty acids deriving from biological sources.

For the purposes of the present invention, with the term "green diesel" it is intended a fuel for diesel engines comprising products of the hydrogenation or deoxygenation of lipids deriving from biological sources in the presence of hydrogen and at least one catalyst.

For the purposes of the present invention, with the wording "oleaginous yeast" it is intended a yeast species which includes, but it is not absolutely limited to, the species of the following genres: *Yarrowia, Candida, Cryptococcus, Trichosporon, Torulopsis, Lipomyces, Rhodotorula* and *Rhodosporidium* and that is capable to accumulate lipids in an amount equal to or higher than 25% of its cell dry-weight.

For the purposes of the present invention, with the term "hyperaccumulator" it is intended an oleaginous yeast variant capable to accumulate lipids in a percentage equal to or higher than 40% referred to its cell dry-weight.

For the purposes of the present invention, the wordings "cultivation" and "culture" indicate the processes through which the cells of a microorganism grow and reproduce in conditions controlled by man. In the processes defined through the above-cited expressions, it is comprised the "fermentation" of the oleaginous yeast, carried out in some embodiments of the invention.

For the purposes of the present invention, the wording "culture medium" indicates a liquid, or a gel, prepared for supporting microorganisms growth, such as, for example, cells of oleaginous yeast. The culture medium may be of defined composition (for example, "YEPD" medium, "B" medium, etc.) or may derive from the treatment of not-selected sources, such as, for example, wastewaters, market waste, or hydrolyzates of lignocellulosic material.

For the purposes of the present invention, with the wordings "a fed-batch system" is intended a semi-continuous fermentation mode of the oleaginous yeast, which allows to extend the time of cell growth before achieving the stationary state through the addition of fresh medium to the culture according to pre-determined parameters.

For the purposes of the present invention, with the wordings "carbon source" "nitrogen source", "sulfur source" and "phosphorous source" is intended organic or inorganic substances, or compositions of said carbon-based, nitrogen-based, sulfur-based substances (for examples, sulfates) and phosphorus (for example, phosphates), respectively, contained in the culture medium and that a microorganism may metabolize for deriving energy.

For the purposes of the present invention, with the term "biomass" is intended all cells produced during fermentations or in the other culture modes. According to some embodiments of the present invention, the biomass may be separated from the culture medium by centrifugation or by microfiltration.

For the purposes of the present invention, with the terms "lignocellulosic material" and "lignocellulosic biomass" is intended a complex structure of vegetal origin comprising cellulose, hemicellulose and lignin. From this material through chemical-physical and enzymatic treatments known in the prior art, sugars which may be used as carbon sources in fermentation processes of microorganisms for the production of alcohols and/or lipids are obtained. For example, according to a method disclosed in the International patent application WO 2012/042544, the lignocellulosic material, after crushing and grinding, is pre-treated in a reactor pressurized with water vapor for a pre-determined time. At the end, after a slow depressurization, the liquid phase enriched in sugars derived from the hydrolysis of hemicellulose is separated. The remaining solid phase is subjected to a new treatment with water vapor in the pressurized reactor. At the end of this second step, the pressure established in the reactor is instantly released, so as to cause the steam explosion in the lignocellulosic biomass cells so disentangling the structure of lignin and cellulose. The obtained material, combined with the liquid phase previously obtained, is then transferred into a bioreactor together with an enzyme suspension that, having more accessibility to the material in view of the preceding pre-treatment, complete the process of polysaccharides hydrolysis. The obtained preparation may be called "lignocellulosic hydrolyzate".

Further characteristics and advantages of the present invention will become apparent from the following detailed description.

The present invention therefore relates to a variant of oleaginous yeast of the species *Rhodosporidium azoricum*, characterized by the intracellular lipid accumulation, deposited at Leibniz-Institut DSMZ—Deutsche Sammlung von Mikroorganismen und Zellkulturen GmbH (DSMZ), Inhoffenstraße 7 B 38124 Braunschweig (Germany), on Oct. 10, 2014, with the deposit number DSM 29495.

According to a preferred embodiment of the present invention this yeast is characterized by an intracellular lipid accumulation in an amount higher or equal to 60% of its cell dry weight, preferably in an amount comprised between 62% and 70%, when cultured in culture media rich in nitrogen sources.

According to a preferred embodiment this yeast is characterized by an intracellular lipid accumulation in an amount higher or equal to 40%, preferably in an amount comprised between 45% and 60% of its cell dry weight when cultured using hydrolyzates of lignocellulosic materials as nutrient sources, preferably when said substrates are hydrolyzate from *Arundo donax* (common cane).

The genotype of the variant strain DSM 29495 was characterized by comparing the sequence of its genomic DNA with the sequence of the wild-type strain of *Rhodosporidium azoricum*, as described in the example 2 reported below.

124 mutations were found. Among this, 116 are included in the genome coding regions, or in the areas adjacent to the coding zones and therefore likely involved in the expression and translation processes in said coding areas (e.g., promoters or intronic sequences), whereas 8 are in the genome putatively non-coding areas. Based on the comparison with the transcribed DNA (or "transcriptoma") of the wild-type strain, it was possible to attribute mutations to 49 genic transcripts, for some of which homologies with genes involved in ubiquitination, glycosylation, ribosylation, redox cofactor recycle (NADH dehydrogenases) processes and with genes of some membrane carrier were observed.

Without being bound by any theory, said mutations (and, among them, in particular mutations in the homozygous form) may explain the different behavior of the variant DSM 29495 with respect to the wild-type strain as, intervening on enzymes responsible of nucleotide cofactor re-oxidation and on systems which act as transcriptional or post-transcriptional regulators, they could indirectly act on the biosynthetic routes which regard lipid production.

In the following Table I mutations detected in the genomic DNA of the variant strain DSM 29495 with respect to the wild-type strain are reported. For each mutation, the position of the so-called "contig" is indicated, namely on one of the contiguous regions of genomic DNA which, assembled according to their nucleotide sequence, allow the genome reconstruction. Furthermore in the table are indicated: the mutation type (SNV: "single nucleotide variation", single nucleotide mutation; MNV: "multiple nucleotide variation", mutation of more nucleotides in sequence; Ins: insertion of one or more nucleotides; Del: deletion of one or more nucleotides), the number of nucleotides involved, the nucleotide or nucleotides varied (by mutation, insertion or deletion) respectively in the genome of the wild type strain and in the genome of the strain DSM 29495, the indication that the mutation is observed in a gene present in single copy (homozygous) or in more copies (heterozygous) in the genome.

TABLE I

| Contigous region | Position | Type | Length | Wild-type | Mut. | Copies |
|---|---|---|---|---|---|---|
| contig_118 (1 . . . 179119) | 88613 | SNV | 1 | G | A | Homozygous |
| contig_125 (1 . . . 6454) | 838 | SNV | 1 | G | A | Heterozygous |
| | 3799 | SNV | 1 | G | A | Heterozygous |
| | 4304 | SNV | 1 | G | A | Heterozygous |
| | 4331 | SNV | 1 | G | A | Heterozygous |
| contig_134 (1 . . . 24300) | 23417 | SNV | 1 | A | G | Homozygous |
| | 23420 | SNV | 1 | T | G | Homozygous |
| | 23417 | SNV | 1 | A | G | Heterozygous |
| | 23420 | SNV | 1 | T | G | Heterozygous |
| | 23746 | SNV | 1 | A | T | Heterozygous |
| | 23985 | SNV | 1 | A | G | Heterozygous |
| | 23995 | SNV | 1 | A | G | Heterozygous |
| contig_135 (1 . . . 78168) | 44534 | SNV | 1 | G | T | Heterozygous |
| | 44537 | SNV | 1 | G | C | Heterozygous |
| | 44549 | SNV | 1 | T | A | Heterozygous |
| | 44552 | SNV | 1 | G | C | Heterozygous |
| | 44688 | SNV | 1 | G | A | Heterozygous |
| | 44691 | SNV | 1 | A | C | Heterozygous |
| | 44697 | SNV | 1 | G | C | Heterozygous |
| | 44701 | SNV | 1 | G | T | Heterozygous |
| | 44981 | SNV | 1 | C | T | Heterozygous |
| | 45008 | SNV | 1 | C | G | Heterozygous |
| | 45047 | SNV | 1 | G | A | Heterozygous |
| | 45059 | SNV | 1 | T | C | Heterozygous |
| | 47692 | SNV | 1 | C | T | Heterozygous |
| | 47707 | SNV | 1 | T | C | Heterozygous |
| | 47904 | SNV | 1 | C | T | Heterozygous |
| | 47917 | SNV | 1 | G | C | Heterozygous |
| | 47935 | SNV | 1 | C | A | Heterozygous |
| | 49371 | SNV | 1 | C | G | Heterozygous |
| | 49377 | SNV | 1 | C | G | Heterozygous |
| | 49383 | SNV | 1 | T | G | Heterozygous |
| contig_147 (1 . . . 47414) | 46833 | SNV | 1 | A | G | Heterozygous |
| | 46971 | SNV | 1 | A | G | Heterozygous |
| | 46973 | SNV | 1 | G | A | Heterozygous |
| contig_148 (1 . . . 52523) | 7780 | SNV | 1 | C | T | Homozygous |
| | 7805 | Del | 3 | TCC | — | Homozygous |
| contig_17 (1 . . . 199344) | 188703 | Ins | 6 | — | ATGCCC | Homozygous |
| contig_217 (1 . . . 91046) | 790 | SNV | 1 | A | G | Heterozygous |
| | 794 | SNV | 1 | G | C | Heterozygous |
| contig_287 (1 . . . 108965) | 10951 | SNV | 1 | C | T | Heterozygous |
| contig_293 (1 . . . 4167) | 432 | SNV | 1 | C | T | Heterozygous |
| | 1565 | SNV | 1 | C | G | Heterozygous |
| | 1930 | SNV | 1 | G | A | Heterozygous |
| | 2318 | SNV | 1 | C | G | Heterozygous |
| | 2652 | Del | 1 | A | — | Homozygous |
| | 2652 | Del | 1 | A | — | Heterozygous |
| contig_311 (1 . . . 2053) | 321 | SNV | 1 | T | C | Homozygous |
| | 321 | SNV | 1 | T | C | Heterozygous |
| contig_324 (1 . . . 40071) | 18905 | SNV | 1 | C | T | Homozygous |
| contig_330 (1 . . . 49930) | 48496 | SNV | 1 | A | G | Heterozygous |
| contig_358 (1 . . . 8393) | 6638 | SNV | 1 | T | C | Heterozygous |
| | 6650 | SNV | 1 | A | C | Heterozygous |
| | 6869 | SNV | 1 | T | C | Heterozygous |
| | 6873 | SNV | 1 | A | G | Heterozygous |
| | 6889 | SNV | 1 | G | C | Heterozygous |
| contig_381 (1 . . . 3531) | 1962 | SNV | 1 | C | A | Heterozygous |
| contig_421 (1 . . . 324) | 183 | SNV | 1 | T | G | Heterozygous |
| | 196 | SNV | 1 | T | C | Heterozygous |
| contig_465 (1 . . . 4081) | 1294 | SNV | 1 | A | G | Heterozygous |
| | 1299 | SNV | 1 | T | C | Heterozygous |
| | 1306 | SNV | 1 | T | A | Heterozygous |
| | 1309 | SNV | 1 | G | A | Heterozygous |
| | 1341 | MNV | 2 | TG | CA | Heterozygous |

TABLE I-continued

| Contigous region | Position | Type | Length | Wild-type | Mut. | Copies |
|---|---|---|---|---|---|---|
| | 1362 | Del | 1 | C | — | Heterozygous |
| | 1370 | SNV | 1 | G | A | Heterozygous |
| contig_467 (1 . . . 7174) | 2721 | SNV | 1 | A | G | Heterozygous |
| | 2683 | SNV | 1 | G | A | Heterozygous |
| | 2690 | SNV | 1 | C | T | Heterozygous |
| | 2698 | SNV | 1 | A | G | Heterozygous |
| contig_468 (1 . . . 895) | 304 | SNV | 1 | G | A | Heterozygous |
| | 331 | SNV | 1 | C | T | Heterozygous |
| | 174 | SNV | 1 | G | A | Heterozygous |
| contig_469 (1 . . . 687) | 338 | MNV | 2 | CA | TG | Heterozygous |
| | 343 | SNV | 1 | A | G | Heterozygous |
| | 359 | SNV | 1 | T | C | Heterozygous |
| contig_51 (1 . . . 125008) | 117390 | SNV | 1 | C | T | Heterozygous |
| | 117400 | SNV | 1 | G | A | Heterozygous |
| | 117407 | SNV | 1 | T | C | Heterozygous |
| | 117409 | SNV | 1 | C | T | Heterozygous |
| | 117418 | SNV | 1 | C | T | Heterozygous |
| | 117579 | SNV | 1 | G | T | Heterozygous |
| contig_56 (1 . . . 124207) | 523 | MNV | 2 | TC | AA | Homozygous |
| | 3297 | SNV | 1 | G | A | Heterozygous |
| | 3299 | SNV | 1 | A | T | Heterozygous |
| | 3446 | SNV | 1 | G | A | Heterozygous |
| | 3515 | SNV | 1 | C | T | Heterozygous |
| | 3681 | SNV | 1 | T | C | Heterozygous |
| | 3689 | SNV | 1 | A | G | Heterozygous |
| | 3693 | SNV | 1 | G | A | Heterozygous |
| | 3702 | SNV | 1 | C | T | Heterozygous |
| contig_595 (1 . . . 265) | 142 | SNV | 1 | A | G | Heterozygous |
| cointig_603 (1 . . . 331) | 172 | SNV | 1 | A | G | Heterozygous |
| contig_673 (1 . . . 205) | 46 | MNV | 2 | TG | CA | Heterozygous |
| contig_733 (1 . . . 347) | 241 | SNV | 1 | G | C | Heterozygous |
| contig_75 (1 . . . 8581) | 2409 | SNV | 1 | C | A | Heterozygous |
| contig_76 (1 . . . 86377) | 468 | SNV | 1 | C | T | Heterozygous |
| | 469 | SNV | 1 | T | C | Homozygous |
| contig_793 (1 . . . 216) | 177 | SNV | 1 | C | T | Heterozygous |
| | 180 | SNV | 1 | C | T | Heterozygous |
| contig_82 (1 . . . 127699) | 50031 | SNV | 1 | T | G | Heterozygous |
| | 50049 | SNV | 1 | T | G | Heterozygous |
| | 50073 | SNV | 1 | C | G | Heterozygous |
| | 50076 | SNV | 1 | G | C | Heterozygous |
| | 50087 | SNV | 1 | G | A | Heterozygous |
| | 50090 | SNV | 1 | A | G | Heterozygous |
| | 48500 | SNV | 1 | G | C | Heterozygous |
| | 48506 | SNV | 1 | G | A | Heterozygous |
| | 48518 | SNV | 1 | C | G | Heterozygous |
| | 48537 | SNV | 1 | A | G | Heterozygous |
| | 48552 | SNV | 1 | C | G | Heterozygous |
| | 48554 | SNV | 1 | A | G | Heterozygous |
| | 48566 | SNV | 1 | A | T | Heterozygous |
| | 48575 | SNV | 1 | G | A | Heterozygous |
| contig_887 (1 . . . 296) | 134 | SNV | 1 | C | G | Heterozygous |
| | 149 | SNV | 1 | C | T | Heterozygous |
| contig_93 (1 . . . 338791) | 4048 | SNV | 1 | T | G | Homozygous |
| contig_99 (1 . . . 119178) | 29299 | SNV | 1 | C | A | Heterozygous |
| | 29307 | SNV | 1 | C | T | Heterozygous |
| | 29310 | SNV | 1 | A | T | Heterozygous |
| | 29320 | SNV | 1 | G | C | Heterozygous |
| | 29336 | SNV | 1 | G | A | Heterozygous |
| | 29341 | SNV | 1 | T | G | Heterozygous |
| | 29349 | SNV | 1 | G | A | Heterozygous |

Lipid accumulation capacity of the variant *Rhodosporidium azoricum* DSM 29495, compared to the wild-type strain, was tested by several experiments, some of which are described in the examples reported below, in which biomass production and the amount of lipids accumulated during the fermentation were determined.

A further aspect of the present invention relates to a method for obtaining oleaginous yeast variants, preferably selected from the species which include *Yarrowia* spp., *Candida* spp., *Cryptococcus* spp., *Trichosporon* spp., *Torulopsis* spp., Lipomyces spp., *Rhodotorula* spp. and *Rhodosporidium* spp., comprising the steps of:

i. exposing the cells of an oleaginous yeast strain to a mutagenic agent in order to generate random mutations in the genomic DNA;

ii. inoculating and cultivating in a culture medium the cells treated with the mutagenic agent, said culture medium being characterized by the presence of at least one carbon source at concentrations comprised between 20 g/L and 100 g/L, preferably between 30 g/L and 50 g/L, and wherein at least one nitrogen source is present, preferably at concentrations comprised between 3 g/L and 40 g/L, more preferably between 5 g/L and 20 g/L;

iii. separating the yeast cells characterized by a lower density from the cell culture.

All the steps of the above-described method are preferably carried out in sterile conditions, in order to avoid culture contamination from microorganisms present in the environment, and more preferably in the described sequence.

According to a preferred embodiment, the cultivation step ii. of said method may be carried out for a time comprised between 16 and 48 hours, at a temperature comprised between 10° C. and 40° C., more preferably between 20° C. and 30° C.

According to a preferred embodiment, step iii. of said method may comprise the sub-steps of:

a) collecting a sample from the culture and adding at least one thickening agent in suitable amount;

b) centrifuging the cell suspension so obtained at low speed;

c) collecting the higher fraction of the centrifugation supernatant in order to isolate cells characterized by lower density from the rest of the cell culture;

d) inoculating and cultivating the fraction of the supernatant isolated in the sub-step c) of said method in a culture medium, characterized by the presence of at least one carbon source at concentrations comprised between 20 g/L and 100 g/L, preferably between 30 g/L and 50 g/L, and wherein at least one nitrogen source is present, preferably at concentrations comprised between 3 g/L and 40 g/L, more preferably between 5 g/L and 20 g/L;

e) repeating the sub-steps from a) to d), for at least 2 times, preferably for at least from 5 to 20 times;

f) isolating single mutant colonies.

Suitable thickeners for the purposes of the present invention are products and mixtures of products adapted to create density gradients by centrifugation and compatible with the survival of the treated microorganism. Such products comprise, preferably, polyhydroxy compounds such as, for example, glycerol, saccharose, sorbitol and dextran, which are used, according to methods known in the prior art, to separate prokaryotic cells, eukaryotic cells, and subcellular components thereof, by density gradient centrifugation.

According to a particularly preferred embodiment of the present invention, the sub-step a) above described may be carried out by adding to the culture sample, as thickener, sorbitol up to a concentration comprised between 1M and 3M.

Noteworthy, the method of this preferred embodiment of the present invention takes advantage of the characteristics of lower density of cells that accumulate high amounts of lipids with respect to cells that accumulate less amounts of lipids for selecting variants of the oleaginous yeast strain which differentiate from the wild type strain for the fact of being able to grow and accumulate lipids in said medium rich in carbon sources and of further nutrients with a higher degree with respect to what occurs in cells of the wild type strain.

According to a preferred embodiment, the cultivation of sub-step d) of said method may be carried out for a time comprised between 16 and 48 hours, at a temperature comprised between 10° C. and 40° C., more preferably between 20° C. and 30° C.

The isolation of the individual mutant colonies [sub-step f)] may be carried out by procedures known in the prior art such as, for example, the serial dilution or the distribution of the cell suspension on a medium containing agar or other solidifying agents.

According to a preferred embodiment of the present invention, the oleaginous yeast used may be *Rhodosporidium azoricum*.

According to a further preferred embodiment of the present invention, the oleaginous yeast mutant obtained by using said method may be the variant of the strain *Rhodosporidium azoricum* DMS 29495.

In fact, it is to be noted that said method was advantageously used to obtain the variant of the strain *Rhodosporidium azoricum* DSM 29495.

The above described method may profitably be used to select variants which accumulate lipids in media rich not only of nitrogen sources, but also of phosphorous and sulfur sources, both inorganic and organic, so as of other items of nutrients that, according to the teachings of the prior art, similarly to what occurs for the nitrogen sources, when present at concentrations suitable for yeast cultivation, even stimulating biomass growth, show an inhibitory effect on the accumulation process of lipids within the microorganism.

According to a preferred embodiment of the present invention, in the culture medium used in said method the at least one nitrogen source may be replaced by at least one sulfur source, organic or inorganic, at concentration comprised between 3 g/L and 40 g/L, preferably between 5 g/L and 20 g/L.

According to a preferred embodiment of the present invention, in the culture medium used in said method the at least one nitrogen source may be replaced by at least one phosphorous source, organic or inorganic, at concentrations comprised between 3 g/L and 40 g/L, preferably between 5 g/L and 20 g/L.

The mutagenesis process according to said method may be carried out according to anyone of the known techniques for this purpose.

According to a particular preferred embodiment of the present invention, the mutagenesis process may be carried out by physical way through the exposition of said yeast strain to the ultraviolet radiation (UV) with a wavelength comprised between 230 and 260 nm.

The mutagenesis by exposition to UV radiation may be carried out as described in the prior art [Winston F. (2008) "*Current Protocols in Molecular Biology*" John Wiley & Sons], and, for example, it may be carried out by exposing yeast cells placed in a Petri plate on a medium solidified with agar and a UV radiation source (represented by at least one lamp with a power comprised between 8 and 15 W with a wavelength comprised between 230 and 260 nm), placed at a distance comprised between 10 and 50 cm from the Petri plates, for a time comprised between 5 seconds and 5 minutes.

According to a further preferred embodiment of the present invention, the mutagenesis process according said method may be carried out by chemical way, adding ethyl mesylate (EMS) at a concentration comprised between 0.1% and 10% (vol/vol) to the culture medium in which the strain to be treated is inoculated and maintaining the culture in the presence of said mutagenic agent for a time comprised between 10 minutes and 12 hours, preferably between 1 hour and 8 hours.

As known to the person skilled in the art, it is possible to obtain an indication about the cell number in the culture by the measure of turbidity, or optical density, of the culture itself at 660 nm (Optical Density, $OD_{660}$); therefore it may be useful for practical purposes defining a determined cell amount in the culture, or a volume of such culture, in terms of $OD_{660}$.

According to a preferred embodiment of the present invention, the culture volume collected during the sub-step a) of said method may correspond to an optical density comprised between 50 $OD_{660}$ and 200 $OD_{660}$, preferably between 80 $OD_{660}$ and 150 $OD_{660}$.

It is to be noted that, during the sub-step a) of said method, as an alternative to the direct addition of the thickener to the collected culture, it is possible to recover the sample cells by centrifugation, resuspend them in a fresh culture medium and to said suspension, the desired amount of thickener may be added.

According to a preferred embodiment of the present invention, the centrifugation during the sub-step b) of said method may be carried out for a time comprised between 1 and 5 minutes at an acceleration comprised between 500 g and 1000 g.

It is to be noted that by repeating the steps from a) to d) of said method for several times, numerous generations of the mutant strain may be obtained, in the order of several tens; that increases the probability that the lipid accumulation is not bound to a remodulation of the protein expression related to culture conditions, but it is a behavior actually imprinted at genetic level. Furthermore, in this way the enrichment of population of possible mutants with the more effective hyperaccumulator is promoted.

The variant strain *Rhodosporidium azoricum* DSM 29495 obtained with the above-described method may be advantageously used for the microbial production of lipids by fermentation processes in conditions that promote the biomass production.

Therefore it is a further embodiment of the present invention a method for producing lipids through the cultivation of the oleaginous yeast variant *Rhodosporidium azoricum* DSM 29495, comprising the steps of:
  i. preparing a culture medium comprising:
    at least one carbon source at concentrations between 20 g/L and 100 g/L, preferably between 30 g/L and 50 g/L;
    at least one nitrogen source, preferably at concentrations comprised between 3 g/L and 40 g/L, more preferably between 5 g/L and 20 g/L;
  ii. cultivating said oleaginous yeast variant in said culture medium;
  iii. separating the yeast cells from the culture medium;
  iv. extracting the intracellular lipids accumulated within the yeast cells.

According to a preferred embodiment of the present invention, the culture may be carried out at a temperature comprised between 10° C. and 40° C., preferably comprised between 20° C. and 30° C.

According to a preferred embodiment of the present invention, the culture may be carried out for a time comprised between 50 hours and 200 hours, preferably comprised between 90 hours and 150 hours.

In a preferred embodiment of the present invention, the culture may be carried out in aerobic condition, by insufflation of sterile air and by variable stirring between 600 and 900 rpm modulated with air flux so as to maintain the dissolved oxygen concentration ($DO_2$) equal to 30% of the saturation value.

According to a preferred aspect of the present invention, the culture may be carried out at a pH value comprised between 4.5 and 7.0, preferably comprised between 5.0 and 6.5. In order to maintain the pH within the desired ranges, an aqueous solution of at least one inorganic base such as, for example, NaOH, KOH, $Ca(OH)_2$, $Mg(OH)_2$ or mixtures thereof, preferably KOH, or an aqueous solution of at least one inorganic acid such as, for example, $H_3PO_4$, $H_2SO_4$, HCl or mixtures thereof, preferably $H_2SO_4$, may be added to the culture medium used for the fermentation, in an amount such that obtaining the desired pH.

In a preferred embodiment of the present invention the culture may be carried out starting from an inoculum in an amount comprised between 1% and 5% (vol/vol) of the total volume of the medium, obtained from a previous culture of said yeast strain carried out in the same medium for a time comprised between 6 and 24 hours.

Said previous culture may be in turn inoculated from an anterior culture or may be inoculated starting from a sample of said yeast strain maintained at −80° C. in a suspension containing 15% (vol/vol)glycerol.

According to a preferred embodiment of the present invention, the culture medium may comprise glucose as carbon source and $(NH_4)_2SO_4$ as nitrogen source.

According to a preferred embodiment of the invention, the culture medium according to said method may comprise a lignocellulosic hydrolyzate as carbon source.

According to a further preferred embodiment of the invention, said lignocellulosic hydrolyzate may derivate from the treatment of:
  a. products deriving from cultures expressly cultivated for energetic use, e.g., species of the genera *Arundo*, *Miscanthus*, *Panicum*, comprising scraps, residues and waste deriving from said products or from the processing thereof;
  b. products deriving from the agriculture, e.g., species of the genera *Carduus*, *Parthenium*, *Zea*, *Glycine*, *Gossypium*, *Linum*, *Brassica*, *Saccharum*, *Elaeis*, *Attalea*, comprising scraps, residues and waste deriving from said products or from the processing thereof;
  c. products deriving from forestation or forestry, comprising scraps, residues and waste deriving from said products or from the processing thereof;
  d. scraps of food and agricultural products for human alimentation or zootechnics;
  e. paper industry residues, non-chemically treated;
  f. waste deriving from the recycling collection of urban solid waste (e.g. of vegetable origin, paper);
  g. algae, e.g. microalgae or macroalgae, in particular macroalgae.

According to a preferred embodiment of the invention, said lignocellulosic hydrolyzate may derivate from the treatment of specimens of the species *Arundo donax* (common cane), comprising scraps, residues and waste deriving from the processing thereof.

According to a further preferred embodiment of the invention, said lignocellulosic hydrolyzate of *Arundo donax* (common cane) may be obtained by hydrothermal treatment ("steam explosion") and subsequent enzymatic hydrolysis.

During the experiments of lipid production into a fermenter, the culture according to said method may be carried out the "fed-batch" mode.

According to a preferred embodiment of the invention, a culture carried out according to said method, grown-up for a time comprised between 12 and 24 hours after the inoculum, may be further carried out in "fed-batch", preferably for a time comprised between 90 hours and 200 hours, more preferably comprised between 100 and 150 hours, by adding an aqueous solution of glucose so as to obtain a stable concentration of glucose in the medium comprised between 25 g/L and 50 g/L.

In a preferred embodiment, a culture carried out according to said method, grown-up for a time comprised between 12 and 24 hours after the inoculum, may be further carried out in "fed-batch", preferably for a time comprised between 90 hours and 200 hours, more preferably comprised between 100 and 150 hours, by adding a lignocellulosic hydrolyzate so as to obtain a stable concentration of total sugars comprised between 25 g/L and 50 g/L.

The cell growth in culture may be measured by spectrophotometric methods determining the turbidity, or optical density (OD) of a culture sample at 660 nm ($OD_{660}$).

At the end of the culture, the variant strain cells of oleaginous yeast Rhodosporidium azoricum DSM 29495 used in the fermentation may be separated from the culture medium through methods known in the prior art such as, for example, filtration, filter-pressing, microfiltration or ultrafiltration, centrifugation.

In order to further concentrate the aqueous suspension of oleaginous cell biomass obtained after separation, said biomass aqueous suspension may be further subjected to centrifugation. Said centrifugation may be carried out for a time comprised between 5 minutes and 30 minutes, preferably comprised between 15 minutes and 25 minutes, at a rotation speed comprised between 3,000 rpm and 9,000 rpm, preferably comprised between 4,000 rpm and 8,000 rpm.

The biomass produced may be measured in grams per liter of culture, determining the dry weight of the yeast cells of a culture sample of known volume collect at predetermined intervals and at the end of fermentation.

In order to recover lipids, the biomass comprising the oleaginous yeast cells obtained may be subjected to cell lysis according to procedures known in the prior art and described, for example, in the international patent application WO2014/102254 among which, for example, the heat treatment in a pressurized reactor, the mechanic treatment with a homogenizer, or the treatment with microwaves.

At the end of said cell lysis, lipids may be recovered from the obtained suspension, through extraction with polar or apolar organic solvents, according to procedures known in the prior art and described for example in the international patent application WO2014/102254.

Lipid production from cells in culture may be measured by colorimetric methods known in the prior art, directly in sample of yeast cell suspension, for example, with sulfo-phospho-vanillin using, for example, the "Total lipids—sulpho-phospho vanillin" kit marketed by Spinreact S.A.U., Ctra. Santa Coloma, 7 E-17176 St. Esteve d'en Bas (GI), Spain.

Furthermore, the lipid amount produced may be determined with gravimetric methods on the fraction extracted with mixtures of organic solvent, for example with chloroform:metanol 2:1, vol/vol [Folch J., Lees M., Sloan-Stanley G. H. (1957), "A simple method for the isolation and purification of total lipids from animal tissues", J. Biol. Chem., vol. 226, p. 497-509] or with n-exane:isopropanol 3:2 vol/vol [Hara A., Radin N. S. (1978), "Lipid extraction of tissues with a low-toxicity solvent", Anal. Biochem., vol. 90, p. 420-426], from samples of lyophilized biomass.

In order to assess the performances relating to lipid accumulation in fermentation of the variant Rhodosporidium azoricum DSM 29495, with respect to the wild-type strain, the biomass dry-weight (expressed in g/L) and lipid amount (expressed in g/L) through the above-listed methods at the end of the culture may be determined and measuring the percentage ratio between these two parameters.

It is to be noted that, in the fermentation conditions according to the method claimed in the present invention, the variant of the species Rhodosporidium azoricum DSM 29495, with respect to the wild type strain of the same species, produces higher yields both in terms of biomass (increase comprised between 13% and 58%) and accumulated lipids (increase comprised between 37% and 65%).

The lipid fraction may be analyzed by chromatographic techniques, for example by gas chromatography or by high performance liquid chromatography (HPLC) according to procedures of the prior art.

By said analytic methods it was detected that lipids accumulated in the oleaginous yeast cells are represented for the 90% by triglycerides, preferably glycerol esters with fatty acids having from 8 to 24 carbon atoms, such as, for example, palmitic acid, stearic acid, oleic acid and α-linoleic acid.

Other lipids which may be present are: phospholipids, monoglycerides, diglycerides, free fatty acids, or mixtures thereof.

Lipids obtained according the process object of the present invention may be advantageously used as synthesis intermediates, particularly in the field of the so-called "green-chemistry". Furthermore, they may be subjected to transesterification in the presence of at least one alcohol having from 1 to 4 carbon atoms, preferably methanol or ethanol, and of at least one acid or basic catalyst, in order to produce glycerol and alkyl esters, particularly methyl esters or ethyl esters ("biodiesel").

Alternatively, said lipids may be subjected to hydrogenation/deoxygenation in the presence of hydrogen and of at least one catalyst in order to produce "green diesel". The hydrogenation/deoxygenation processes are known in the prior art and are disclosed, for example, in the European patent application EP 1,728,844.

In order to realize the present invention and better illustrate the same, some non-limiting examples are reported below.

EXAMPLE 1 (OBTAINMENT OF THE VARIANT RHODOSPORIDIUM AZORICUM DSM 29495)

Following it is reported a practical example of the method for obtaining variant strains of the wild-type strain of the species Rhodosporidium azoricum, through which the variant deposited at Leibniz-Institut DSMZ, with the deposit number DSM 29495, was obtained.

In such example, the random mutagenesis was obtained by UV irradiation.

A cell sample of a wild-type strain of the species Rhodosporidium azoricum was inoculated in the "YEPD" medium (yeast extract 10 g/L, Peptone 10 g/L, glucose 20 g/L) up to achieving the growth exponential phase (10 $OD_{660}$). After, cells were collected by centrifugation at 1500 g for 5 minutes, washed in sterile water, then resuspended in 1 mL of sterile water and placed on the bottom of an empty Petri plate.

Cells placed on the plate were exposed to a source of ultraviolet radiation, represented by a UV lamp of 15 Watt (wavelength 254 nm), put at a distance of 30 cm, for a time equal to 20 seconds, in order to obtain a residue vitality rate of 10%. After that cells were collected from the plate and used to inoculate a liquid culture of yeast cells in medium "B" (yeast extract 1 g/L, $KH_2PO_4$ 1 g/L, $MgSO_4.7H_2O$ 0.05 g/L, NaCl 0.01 g/L $CaCl_2.2H_2O$ 0.01 g/L) containing $(NH_4)_2 SO_4$ 5 g/L and such culture was incubated at 30° C. for 24 hours.

After, a volume of culture equivalent to 100 $OD_{660}$ was collected and cells, recovered by centrifugation, were resuspended in 5 mL of medium "YEPD". To this volume, 5 mL of a sterile solution of sorbitol 2M was added and the so obtained cell suspension was centrifuged for 1 minute at 500 g. After centrifugation 1 mL of suspension was sterilely collected from the higher fraction of supernatant, so isolating in this way those cells with the highest lipid content, less dense, than those cells without lipids (or with lipids accumulated in lower amount) denser, which so are located in the lower portion of the supernatant and in the centrifugation sediment. The collected sample was used to inoculate a new liquid culture. This culture series and isolation of the less dense fraction through centrifugation in a density gradient was repeated for 8 cycles, therefore the culture was spread on "YEPD" medium containing agar, in order to isolate single yeast colonies.

EXAMPLE 2 (GENOTYPIC CHARACTERIZATION OF THE VARIANT RHODOSPORIDIUM AZORICUM DSM 29495)

In the present example the characterization process of the variant *Rhodosporidium azoricum* DSM 29495 is described, by sequencing of the genomic DNA and bioinformatic analysis of mutations present in comparison with the sequence of the genomic DNA of the wild-type strain of the same yeast species.

The genomic DNA was extracted from cultures of both strains (variant DSM 29495 and the wild-type strain) carried out in the medium "YEPD" (yeast extract 10 g/L, Peptone 10 g/L, glucose 20 g/L) for one night, and purified with the commercial kit DNeasy Blood & Tissue kit from Quiagen (cat. Num. 69504) following the instructions provided by the producer.

After checking the purity and integrity degree by electrophoresis, the genomic DNA of each strain was treated separately with the kit "TruSeq DNA Library Preparation Kit" by Illumina, by following the protocol combined with the kit. Briefly, DNA was processed in order to obtain fragments of dimensions comprised between 200 and 400 bp, then bound to 3' and 5' terminus to oligonucleotide adapters provided with the kit and them amplified by "Polymerase Chain Reaction" (PCR) by using as primer the same oligonucleotides. The products of gene amplification were quantified and checked with the device Bioanalyzer 2100 by Agilent Technology. Of each fragment obtained the DNA sequence was determined by using the HiSeq2500 sequencer by Illumina and the obtained sequences were optimized based on "phred" value [Ewing B., Hillier L., Wendl M. C., Green P. (1998), "Base-calling of automated sequencer traces using phred. I. Accuracy assessment". *Genome Res.* 8 (3): 175-185]. The sequence analysis allowed the identification of 893 contiguous regions ("contigs") of dimensions ranging from 120 to 440,000 bp, for a total of 22,722,315 bp. This value is in line with the dimension of the genomic DNA of yeasts filogenetically similar to the genus *Rhodosporidium*, therefore it is believed that the obtained libraries represent the complete genome of *Rhodosporidium azoricum* DSM 29495 and of the correspondent wild-type strain. Sequences of the two genomic DNAs were compared each other by using the software "Map Reads to Reference" and "Quality-based Variant Detection" by CLCbio.

The identified mutations were confirmed by verifying their presence in both sequencing directions and determining the accuracy through the "phred" value.

Overall in the genomic DNA of the variant of *Rhodosporidium azoricum* DSM 29495, 124 mutations were pointed out (comprising substitutions, deletions and nucleotide insertions) reported in Table I.

EXAMPLE 3 (CULTURE IN FLASK)

In this example, performances in terms of growth and lipid accumulation of the yeast variant strain *Rhodosporidium azoricum* DSM 29495 in a medium enriched in nitrogen sources, compared with a wild-type strain of the same species, were assessed. In two sterile flasks of 500 mL, 100 mL of culture medium "B" were put (yeast extract 1 g/L, $KH_2PO_4$ 1 g/L, $MgSO_4.7H_2O$ 0.05 g/L, NaCl 0.01 g/L $CaCl_2.2H_2O$ 0.01 g/L) containing $(NH_4)_2SO_4$ 5 g/L and its pH was adjusted at pH 6.0 by adding of the buffer MES 0.1 M.

In both flasks the culture medium was inoculated with a culture of the variant yeast strain *Rhodosporidium azoricum* DSM 29495 or of the wild-type strain of the same species, both preventively carried out in the medium "B" for about 24 hours, and inoculated in turn with samples of the two yeast strains maintained at −80° C. in a suspension containing glycerol 15% (vol/vol). The inoculated culture volume is settled in order to initially obtain 0.1 $OD_{660}$.

After about 70 hours, after 90 hours and then 114 hours of growth, a culture sample was collected from both flasks and on such sample the biomass was determined (expressed as dry-weight of cells in g per liter of culture) and the amount of the accumulated lipids (expressed as lipid concentration in g/L of the culture and as percentage ratio between lipid weight and the total cells dry-weight).

The analysis results are reported in Table II.

TABLE II

| Strain | Culture-time at the moment of sampling | Dry-weight (g/L culture) | Lipids (g/L culture) | Lipids % |
| --- | --- | --- | --- | --- |
| *Rhodosporidium azoricum* wild-type | 66 hours | 11.17 | 2.58 | 23 |
|  | 90 hours | 14.80 | 3.75 | 25 |
|  | 114 hours | 15.15 | 3.97 | 26 |
| *Rhodosporidium azoricum* DSM 29495 | 71 hours | 12.40 | 3.62 | 29 |
|  | 90 hours | 15.08 | 4.88 | 32 |
|  | 114 hours | 17.18 | 7.33 | 43 |

EXAMPLE 4 ("FED-BATCH" CULTURE)

In this example growth and lipid accumulation of the yeast variant strain *Rhodosporidium azoricum* DSM 29495 was assessed, compared with the wild-type strain of the same species, in a "fed-batch" fermentation.

In order to prepare the fermentation inoculum, 100 mL of "YEPD" medium (yeast extract 1 g/L, Peptone 10 g/L and glucose 20 g/L) were put in two 500 mL flasks.

Then, the culture medium was inoculated with cultures of the variant yeast strain *Rhodosporidium azoricum* DSM 29495 or of the wild-type strain of the same species, preventively carried out in the "YEPD" medium for about 12 hours, and inoculated in turn with samples of the two yeast strains maintained at −80° C. in a suspension containing glycerol 15% (vol/vol). The culture volume inoculated is settled in order to initially obtain 0.1 $OD_{660}$.

The cultures were incubated at 30° C. under stirring for 24 hours.

Cell suspensions obtained were used to separately inoculate fermenters of 20 L, in which 6 L of medium containing glucose 50 g/L, Corn Steep Solid 5 g/L, yeast extract 2 g/L, $KH_2PO_4$ 6 g/L, $MgSO_4.7H_2O$ 0.3 g/L, NaCl 0.06 g/L $CaCl_2.2H_2O$ 0.06 g/L and $(NH_4)_2SO_4$ 5 g/L were placed.

The inoculum volume for each strain is that one necessary to obtain about 6 L of cell suspension having 0.4 $OD_{660}$. For the following growth phase in the "fed-batch" mode, each fermenter is fed with an aqueous solution of glucose 600 g/L according to the consumption kinetics of the carbon source from the two yeast strains, so as to maintain a stable concentration of glucose in the cultures equal to 30 g/l.

The growth occurred in aerobic conditions by air flow and variable stirring between 600 and 900 rpm modulated with the air flux so as to maintain the concentration of dissolved oxygen ($DO_2$) equal to 30% of the saturation value, and at a pH of about 5.0, maintained through the addition, when necessary, of some drops of a solution of KOH 5 M or $H_2SO_4$ 10% (vol/vol).

After 77 hours and after 140 hours of growth, from both the fermenters a culture sample was collected and on such samples the analyses described in the example 3 were carried out.

The results of the analysis are reported in Table III.

TABLE III

| Strain | Culture-time at the moment of sampling | Dry-weight (g/L culture) | Lipids (g/L culture) | Lipids % | Productivity (g/L*h) |
|---|---|---|---|---|---|
| Rhodosporidium azoricum wild-type | 77 hours | 70.80 | 22.80 | 32.20 | 0.29 |
|  | 140 hours | 76.10 | 34.80 | 45.70 | 0.24 |
| Rhodosporidium azoricum DSM 29495 | 77 hours | 64.90 | 33.10 | 51.00 | 0.43 |
|  | 140 hours | 95.30 | 61.80 | 64.90 | 0.44 |

Data reported in this table clearly demonstrate that the variant of *Rhodosporidium azoricum* DSM 29495, in the fermentation conditions described, produces and accumulates lipids in amounts significantly higher than the wild-type strain.

EXAMPLE 5 ("FED-BATCH" CULTURE BY USING A LIGNOCELLULOSIC HYDROLYZATE OF *ARUNDO DONAX* AS A NUTRIENT)

In this example the production of biomass and lipid accumulation of the variant strain of the yeast *Rhodosporidium azoricum* DSM 29495 in a "fed-batch" fermentation was assessed, in which as growth substrate the lignocellulosic hydrolyzate deriving from the hydrothermal and enzymatic treatment of *Arundo donax* was used, compared to the wild-type strain of the same species.

The composition of the hydrolyzate of *Arundo donax* used comprises glucose 224.75 g/L, xylose 107.19 g/L, arabinose 3.94 g/L, cellobiose 16.65 g/L, glycerol 4.24 g/L acetic acid 9.80 g/L, 5-hydroxymethyl-furfural 0.74 g/L and a concentration of total nitrogen equal to 3.69 g/L. The analytic procedures are analogues to those described in the international patent application WO2014/102254.

The total nitrogen was determined by TOC/TN analyzer equipped with gas infrared detector (NDIR, non-dispersive infrared) and using the method of the catalytic oxidation developed by Shimadtzu.

In order to prepare the fermentation inoculum, in two flasks of 2 L, 600 mL of medium consisting of a mixture of 560 mL of "YEPD" medium (yeast extract 1 g/L, peptone 10 g/L and glucose 20 g/L) and 40 mL of lignocellulosic hydrolyzate from *Arundo donax* were predisposed.

The culture medium was inoculated with 10 mL of cultures of the variant yeast strain *Rhodosporidium azoricum* DSM 29495 or of the wild type strain of the same species, preventively carried out in the "YEPD" medium for about 12 hours, and inoculated in turn with samples of the two yeast strains maintained at −80° C. in suspension containing glycerol 15% (vol/vol).

The culture were incubated at 30° C. under stirring for 24 hours.

A volume equal to 550 mL of each cell suspension was separately inoculated in two fermenters in which a fermentation medium with the following composition was predisposed: lignocellulosic hydrolyzate of *Arundo donax* 127 mL/L, yeast extract 2 g/L, Corn Steep Liquor 3 g/L, $KH_2PO_4$ 6 g/L, $MgSO_4.7H_2O$ 0.3 g/L, NaCl 0.06 g/L $CaCl_2.2H_2O$ 0.06 g/L e $(NH_4)_2SO_4$ 4 g/L.

For the next step of growth, in each fermenter the lignocellulosic hydrolyzate from *Arundo donax* according to the consumption kinetics of the carbon source from the two yeast strains was fed, in order to maintain a constant concentration of glucose in the cultures equal to 30 g/L. As the hydrolyzate from *Arundo donax* had a total nitrogen content equal to 3.69 g/L, the feeding also brought such nutritional source to the culture in the fermenter.

The growth was carried out in aerobic conditions, by air insufflation and stirring ranging from 600 to 900 rpm, modulated with an air flux so as to maintain the concentration of dissolved oxygen ($DO_2$) equal to 30% of the saturation value, and at pH equal to 6.0, maintained through the addition, when it is necessary, of some drops of a solution of KOH 5 M or $H_2SO_4$ 10% (vol/vol).

After 74 hours and after 144 hours of growth, a culture sample was collected from both the fermenters and on said samples the analyses described in the example 3 were carried out.

The results of the analyses were reported in Table IV.

TABLE IV

| Strain | Culture-time at the moment of sampling | Dry-weight (g/L culture) | Lipids (g/L culture) | Lipids % | Productivity (g/L*h) |
|---|---|---|---|---|---|
| Rhodosporidium azoricum wild-type | 74 hours | 44.90 | 10.90 | 24.30 | 0.15 |
|  | 144 hours | 46.40 | 15.20 | 32.80 | 0.11 |
| Rhodosporidium azoricum DSM 29495 | 74 hours | 56.00 | 21.25 | 38.30 | 0.29 |
|  | 144 hours | 73.30 | 33.10 | 45.20 | 0.23 |

The invention claimed is:

1. A method for obtaining an oleaginous yeast variant, comprising:
 i. exposing one or more cells of an oleaginous yeast strain to a mutagenic agent in order to generate random mutations in genomic DNA of the cells;
 ii. inoculating and cultivating in a culture medium the cells treated with the mutagenic agent, wherein the culture medium comprises a carbon source at a concentration from 20 g/L to 100 g/L, wherein at least one nitrogen source is present; and
 iii. separating yeast cells having a lower density from the cell culture;
 wherein step (iii) of said method comprises the sub-steps of:
  a) collecting a sample from the culture and adding at least one thickening agent in a suitable amount, to obtain a cell suspension;
  b) centrifuging the cell suspension for a time of 1 to 5 minutes at an acceleration of 500 g to 1000 g, to obtain a centrifugation supernatant;
  c) collecting a higher fraction of the centrifugation supernatant in order to isolate one or more cells characterized by lower density from the rest of the cell culture;

d) inoculating and cultivating the fraction of the supernatant isolated in c) in a culture medium, comprising a carbon source at a concentration from 20 g/L to 100 g/L, wherein at least one nitrogen source is present at a concentration from 3 g/L to 40 g/L;

e) repeating a) to d) at least 2 times, and f) isolating one or more single mutant colonies, and wherein the sub-step a) is carried out by adding sorbitol to the culture sample, as a thickening agent, up to a concentration of 1M to 3M.

2. The method according to claim 1, wherein the inoculating and cultivating of ii. is performed for a time of 16 to 48 hours, at a temperature of 10° C. to 40° C.

3. The method according to claim 1, wherein the inoculating and cultivating of d) is performed for a time of 16 to 48 hours, at a temperature of 10° C. to 40° C.

4. The method according to claim 1, wherein the oleaginous yeast is *Rhodosporidium azoricum*.

5. The method according to claim 1, wherein the oleaginous yeast variant obtained is a variant of the strain *Rhodosporidium azoricum* DMS 29495.

6. The method according to claim 1, wherein mutagenesis occurs:

i. physically, through exposure of the yeast strain to ultraviolet radiation with a wavelength of 230 to 260 nm; or ii. chemically, through exposure to ethyl mesylate at a concentration of 0.1% to 10% (vol/vol) in the culture medium where the strain is inoculated and maintaining the culture in the presence of the mutagenic agent for a time of 10 minutes to 12 hours.

7. The method according to claim 1, wherein the optical density of the sample collected from the culture volume during a) is from 50 $OD_{660}$ to 200 $OD_{660}$.

* * * * *